(12) United States Patent
Ruddle

(10) Patent No.: US 8,388,345 B2
(45) Date of Patent: Mar. 5, 2013

(54) METHOD FOR CLEANING A ROOT CANAL SYSTEM

(76) Inventor: Clifford J. Ruddle, Santa Barbara, CA (US)

( * ) Notice: Subject to any disclaimer, the term of this patent is extended or adjusted under 35 U.S.C. 154(b) by 508 days.

(21) Appl. No.: 12/624,225

(22) Filed: Nov. 23, 2009

(65) Prior Publication Data

US 2010/0092922 A1 Apr. 15, 2010

Related U.S. Application Data

(63) Continuation-in-part of application No. 11/227,934, filed on Sep. 15, 2005, now Pat. No. 8,235,719, which is a continuation-in-part of application No. 11/104,678, filed on Apr. 13, 2005, now abandoned.

(51) Int. Cl.
*A61C 5/02* (2006.01)

(52) U.S. Cl. .......................... 433/224; 433/81

(58) Field of Classification Search ................. 433/102, 433/224, 81, 166, 216
See application file for complete search history.

(56) References Cited

U.S. PATENT DOCUMENTS

| | | | |
|---|---|---|---|
| 4,330,278 A * | 5/1982 | Martin | 433/81 |
| 4,832,061 A | 5/1989 | Hwang | |
| 5,725,370 A | 3/1998 | Himeno et al. | |
| 5,752,825 A * | 5/1998 | Buchanan | 433/32 |
| 5,775,346 A | 7/1998 | Szyszkowski | |
| 5,775,902 A | 7/1998 | Matsutani et al. | |
| 5,868,570 A | 2/1999 | Hickok et al. | |
| 5,899,693 A | 5/1999 | Himeno et al. | |
| 5,952,605 A | 9/1999 | Sievers et al. | |
| 6,059,570 A | 5/2000 | Dragan et al. | |
| 6,085,761 A | 7/2000 | Inaba | |
| 6,162,202 A | 12/2000 | Sicurelli et al. | |
| 6,179,617 B1 | 1/2001 | Ruddle | |
| D441,141 S | 4/2001 | Shalita | |
| 6,290,503 B1 | 9/2001 | Lemon et al. | |
| 6,343,929 B1 | 2/2002 | Fischer | |
| 6,464,498 B1 * | 10/2002 | Pond | 433/81 |
| 6,634,051 B1 | 10/2003 | Dragan et al. | |
| 6,638,067 B2 | 10/2003 | Fischer et al. | |
| 6,981,869 B2 | 1/2006 | Ruddle | |
| 2002/0172922 A1 | 11/2002 | Mannschedel | |
| 2003/0130626 A1 | 7/2003 | VanTassel et al. | |
| 2003/0152886 A1 | 8/2003 | Houdt | |

(Continued)

OTHER PUBLICATIONS

R. Gutaris, et al., In Vivo Debridement Efficacy of Ultrasonic Irrigation Following Hand-Rotary Instrumentation in Human Mandibular Molars, JOE vol. 31, No. 3 pp. 166-170, Mar. 2005.

(Continued)

*Primary Examiner* — Heidi M Eide
(74) *Attorney, Agent, or Firm* — Polster, Lieder, Woodruff & Lucchesi, L.C.

(57) ABSTRACT

An endodontic activator is provided to facilitate the removal of pulp tissue, the smear layer, bacteria and related irritants from a root canal system. The activator is a sonically driven activator made from a strong, flexible, non-metallic, and non-cutting material. The activator can be smooth, flocked or brush-like. The activator comprises a snap-on coupler which is adapted to attach the tool to a driver without the use of tools. The activator can be provided with fluid passages which allow for irrigating reagents to be delivered into or vacuumed from the root canal space during endodontic procedures. By inducing sonic vibrations in the activator, hydrodynamic phenomena are induced in the solution in the root canal to enhance deep lateral cleaning of the root canal system of the tooth.

19 Claims, 4 Drawing Sheets

U.S. PATENT DOCUMENTS

| | | |
|---|---|---|
| 2003/0207231 A1 | 11/2003 | Nance |
| 2004/0126732 A1 | 7/2004 | Nusstein |
| 2004/0126738 A1 | 7/2004 | Atkin et al. |
| 2004/0214135 A1 | 10/2004 | Ruddle |
| 2005/0008673 A1 | 1/2005 | Snyder et al. |
| 2005/0136375 A1* | 6/2005 | Sicurelli et al. ............... 433/81 |
| 2006/0234183 A1 | 10/2006 | Ruddle |
| 2006/0257819 A1* | 11/2006 | Johnson ........................ 433/86 |

OTHER PUBLICATIONS

Sicurelli, et al., Unpublished U.S. Appl. No. 10/741,175, filed Dec. 20, 2003 and entitled "Method and Apparatus to Remove Macro and Micro Debris From a Root Canal".

Cohen and Burns, Pathways of the Pulp, (2002) pp. 261-262.

* cited by examiner

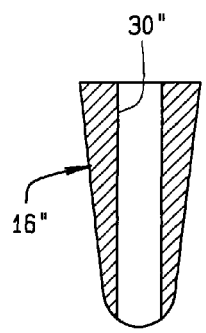 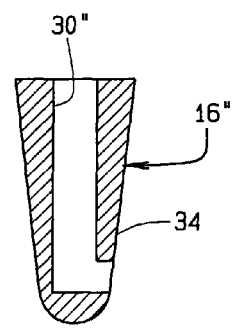
FIG.6A  FIG.6B
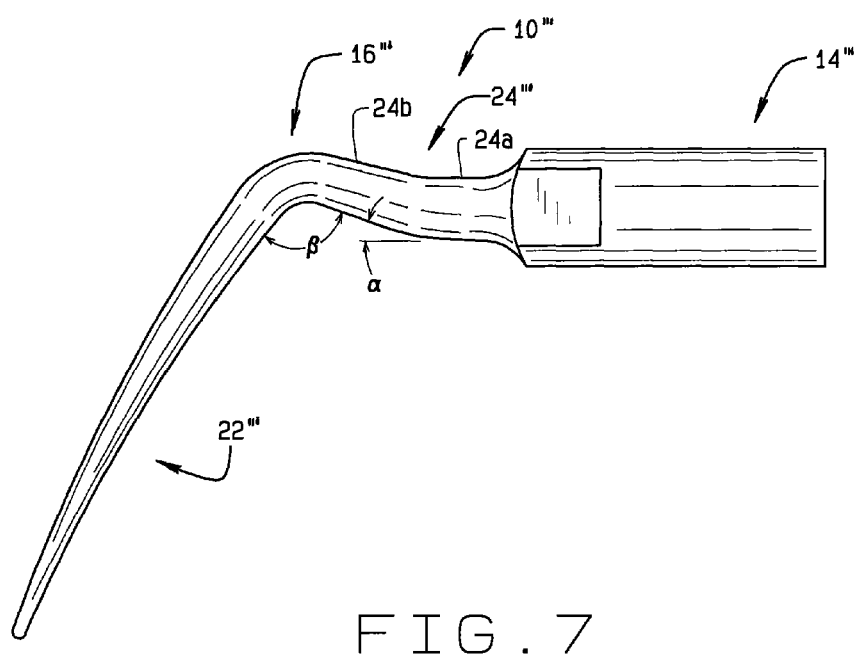
FIG.7

METHOD FOR CLEANING A ROOT CANAL SYSTEM

CROSS-REFERENCE TO RELATED APPLICATIONS

This application is a continuation-in-part of co-pending application Ser. No. 11/227,934 filed Sep. 15, 2005, which, in turn, is a continuation-in-part of application Ser. No. 11/104,678 filed Apr. 13, 2005, now abandoned. Both of said applications are entitled "Apparatus For Cleaning A Root Canal System" and both are incorporated herein by reference.

STATEMENT REGARDING FEDERALLY SPONSORED RESEARCH OR DEVELOPMENT

Not Applicable.

BACKGROUND OF THE INVENTION

This invention relates to endodontic tools, and in particular, to tools used during and after an endodontic root canal preparation procedure, to more effectively clean the root canal system prior to obturation.

Following tooth maturation, the dental pulp is harbored within the structural elements of the tooth. Frequently, and for a variety of reasons, the pulp is irreversibly injured, resulting in inflammatory and infectious conditions which often adversely affect the tooth, its supporting structures, and the patient's health. Clinically, as an alternative to extraction, root canal treatment is performed and ideally directed towards the elimination of pulp, bacteria, if present, and their related irritants from the root canal system, followed by three-dimensionally filling of the root canal space with an inert, biocompatible, dimensionally stable, filling material, such as gutta percha. Ideally, the obturation procedures will fill not just the main canal, but the fins, webs, cul-de-sacs, lateral canals, and all the portals that communicate from the root canal system to the tooth's attachment apparatus.

Root canal procedures are common. Central to a successful endodontic treatment has been the use of chemical reagents during mechanical root canal shaping procedures (i.e., chemomechanical debridement) to completely clean all aspects of the root canal system. Chemicals and traditional methods used to enhance canal debridement and disinfection during cleaning and shaping procedures are limited by many factors that influence their potential to reach all aspects of the root canal system. The most popular chemicals currently used during canal preparation to actively assist in cleaning and disinfecting include bleach, hydrogen peroxide, and chelating agents, such as ethylenediaminetetracetic acid (EDTA) or citric acid. Often, a 6% solution of a clear, pale, greenish-yellow strongly alkaline bleach solution or sodium hypochlorite (NaOCl) and a 17% solution of EDTA are used.

During canal preparation, a solution of NaOCl is liberally irrigated into the root canal space where its solvent action facilitates the digestion and removal of pulp, bacteria, viruses, spores, endotoxins and other irritants generated by the microorganisms. This solution has the potential to circulate, penetrate and, hence, clean into all aspects of the root canal space. However, studies have shown that even the most thorough use of sodium hypochlorite does not remove all the material from the complex anatomy comprising a root canal. The walls of a root canal are comprised of dentin, which contains millions of dentinal tubules per square millimeter. Instruments used to negotiate and shape a canal cut dentin and produce debris which, in the presence of a solution, forms dentinal mud. In combination, dentinal mud, pulp tissue, and when present, bacteria, and their related irritants have been consistently visualized histologically after cleaning and shaping procedures in the dentinal tubules and various aspects of the root canal systems. Thus, after shaping procedures, the walls of the root canal are still covered with a film of debris, frequently described in the literature as a "smear layer." This "smear layer" includes dentinal mud and potentially the organic debris, including the irritants noted above.

After shaping and cleaning procedures, the root canal has been traditionally filled with gutta percha and a root canal cement or sealer. However, if the smear layer or film is not adequately removed from the root canal, the smear layer can compromise the filling and sealing of the root canal system. If obturation is incomplete then the root canal space is predisposed to bacterial leakage and failure. Post-treatment failures attributable to leakage are common and require endodontic retreatment of the tooth or extraction. Thus, for a complete and thorough cleaning, this smear layer or film should be removed. Practitioners use a weak acid or surfactant, such as 17% EDTA, in an effort to remove the smear layer. Typically, the root canal is flushed with EDTA, or other similar reagents, to accomplish this. However, mere flushing of the canal with irrigating solutions does not effectively remove the smear layer from the canal. Some practitioners have used metal cutting files, metal non-cutting files, or metal cannuli (or needle) to activate the solution and enhance the performance of any given reagent. Traditionally, metal cutting and metal non-cutting files or cannula were manually activated. More recently, the metal cutting files, metal non-cutting files, and metal cannuli have been adapted to be connected to a handpiece to be vibrated sonically or ultrasonically.

When using vibratory energy, a sinusoidal shaped wave of piezoelectric energy passes along the length of any given metal object with a given frequency. This wave of modulation produces a characteristic pattern of nodes and antinodes along the length of the vibrated instrument. Because of the manner in which ultrasonic energy is transported, if the instrument contacts a surface, its back and forth movement will be limited and the desired ultrasonic energy will be reduced or dampened. Because virtually all root canals exhibit varying degrees of curvature along their lengths, it is impractical to think one skilled in the art could pass a vibrating file through the length of a root canal without touching the walls of the root canal. If an ultrasonically activated metal object touches a canal wall, then energy is significantly dampened and does not effectively reach the end of the file. Thus the distal end of the ultrasonically activated metal files (whether cutting or non-cutting) or metal cannuli will not vibrate sufficiently to induce hydrodynamic action in the reagent. Hence, the ultrasonic activation of metal instruments is limited in its ability to clean the root canal. Further, the use of ultrasonically driven metal instruments frequently leads to iatrogenic events, such as broken instruments, ledges in the wall of the root canal preparation, apical transportations or even perforations of the root canal. Hence, the use of ultrasonically activated metal devices contributes to undesirable iatrogenic events and dampening of the critical back and forth vibrational movement of any given device which is essential for cleaning. Ultrasonic or piezoelectric energy in curved canals frequently leads to the noted iatrogenic events, which can require corrective non-surgical retreatment, surgeries or extractions.

In my prior U.S. Pat. No. 6,179,617, which is incorporated herein by reference, I disclosed an endodontic brush for use in removing the smear layer. The brush is comprised of a handle, a shank and a brush section extending from the shank. The brush section includes a plurality of bristles extending from a twisted wire core. While this brush works acceptably, it still has many shortcomings which are due to the fact that the core and shank are disclosed to be made from wire. The two twisted wires which form the core and shank are each 0.2 mm in diameter, and hence, the core and shank have a combined diameter of at least 0.4 mm. While the wires are quite thin, even without bristles, the device, at times, has a diameter that is too large to reach the end of smaller diameter canals. From a technical standpoint, the wires cannot be made much thinner because the brush would then become predisposed to breakage during use. Even at the current diameter, the wire shank and core are too flexible. Because of its high flexibility, a dentist cannot effectively and purposely brush the sides of the root canal wall, and hence is limited in the ability to remove the smear layer from the root canal preparation. Additionally, because of the twisted wire core, the brush cannot be driven vibrationally. The twisted wire core prevents the transfer of vibrational energy to the bristles of the brush.

Since the brush may be too large for well-prepared, yet smaller diameter canals, I have encountered another limitation; namely that when the brush is placed into the canal, the reagent or solution in the canal is partially displaced by the brush. This is undesirable as it is through the use of various irrigants that dentists remove the pulp, bacteria when present and their related irritants, and the smear layer from the root canal system.

Additionally, prior sonically or ultrasonically driven endodontic tools require that the tool be threadedly attached to a driver by means of wrenches. This threaded connection makes it time consuming to change tools during a procedure. It would be desirable to make it easier to both attach and remove the tools from their drivers.

BRIEF SUMMARY OF THE DISCLOSURE

Briefly stated, an endodontic tool or activator is provided to facilitate the removal of the smear layer and organic debris from the root canal system after an access cavity to the root canal has been formed, the root canal orifices have been exposed, and the canals shaped to substantially remove organic materials from the primary root canal. The activator comprises a cup-shaped guard, a snap-on coupler, and an active portion extending from the coupler. The coupler is adapted to snap on and be directly connected to the driver. By enabling the activator to be snapped onto a driver, the activator can be connected to its driver without the use of tools (such as wrenches), as is required by the threaded connection. The activator can also be adapted to be connected to the driver by other means, such as a latch-type connection, a frictional connection, a chuck grip connection, etc.

The activator is made from a flexible, non-cutting material. The activator can be made from a non-metal material, such as nylon, Delrin®, or other suitable polymer material. The activator can be generally straight (for connection to a contra-angled handpiece) or it can be contra-angled (for connection to a straight handpiece). The activator comprises an active portion (which is vibrated by the driver) and a working portion which is inserted into the tooth. Depending on the overall length of the canal, the active portion can be inserted deeper into the tooth to allow the working portion to reach the full working length of the canal. The active portion can be substantially parallel (i.e., generally cylindrical) or tapered in design. The surface of the working portion of the activator can be smooth or brush-like. The activator is narrow at its apical or distal end and can have diameters as small as about 0.1 mm to about 0.2 mm at its apical or distal end. At its largest diameter, the coronal or proximal end of the working portion of the activator can have a diameter of about 1 mm. Of critical importance, this size allows for the distal tip of the activator to reach to the end of any prepared root canal. The active portion, if tapered, has a taper of between about 0.01 mm/mm and about 0.12 mm/mm.

In one variation of the activator, the activator includes a flow passage comprised of a generally axially extending central flow channel. The central flow channel may extend over a portion of the length of the activator or may extend along the overall length of activator. Further, the flow passage can include one or more lateral pores (or exits) extending from the central flow channel to the external surface of the activator to deliver any given irrigant to the lateral walls of a root canal. The pores are formed in the working portion of the activator only. If there are a plurality of pores, then the pores can have a diameter substantially smaller than the diameter of the central flow channel. Thus, for example, the pores can have a diameter of about 0.001 mm to about 0.2 mm and the central flow channel can have a diameter of about 0.1 mm to about 1.0 mm, depending on the overall cross-sectional size of the activator. The channel extends through the activator, the entrance to the channel being at the more proximal end of the activator. In one variation, the pores do not extend to the very distal end of the working portion. Thus, for example, the working portion could be free of pores between, for example, $D_0$ and $D_1$. In another variation, the working portion can be provided with pores which extend over the full length of the working portion. In this variation, the pores can have decreasing or increasing diameters over the length of the working portion of the activator to desirably regulate the flow of any given reagent into the root canal.

In use, the method of cleaning a root canal system using the activator comprises (1) preparing an access cavity in the patient's tooth; (2) identifying the orifice(s) of the root canal system within the pulp chamber of the tooth; (3) negotiating and preparing a canal to remove the pulp, and if present, bacteria and related irritants from the root canal; (4) placing an irrigating solution in the root canal; (5) inserting the activator into solution in the canal; and (6) inducing sonic vibrations through the overall length of the activator to initiate a hydrodynamic action in the solution in the root canal to effectively move the solution(s) into the deep lateral anatomy of the root canal which will serve to clean the deep lateral anatomy of the root canal system. If the activator is provided with a flow passage as described above, the method additionally includes passing fresh irrigating solution through the flow passage; thus refreshing the irrigating solution within the root canal space while the energized tip is oscillating within the root canal. Additionally, the flow passage can allow for spent solution to be vacuumed or suctioned from the root canal when the activator is connected to a vacuum source.

BRIEF DESCRIPTION OF THE SEVERAL VIEWS OF THE DRAWINGS

FIGS. 6A and B are enlarged cross-sectional views of the working portion of the activator showing further variations in the flow passage configurations;

FIG. 7 is a side elevational view of the activator formed as a contra-angled tool.

Corresponding reference numerals will be used throughout the several figures of the drawings.

DETAILED DESCRIPTION OF THE INVENTION

Figures 1, 1A:
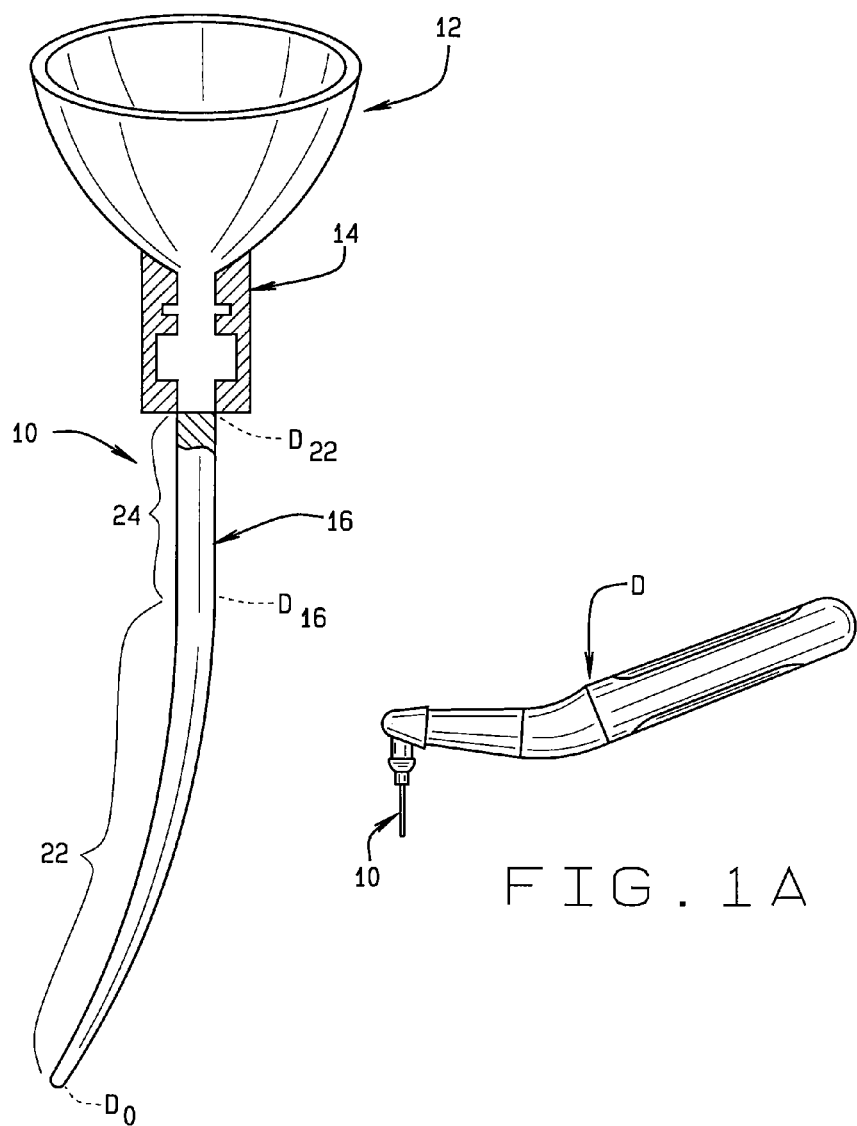
FIG. 1 is an elevational view of an illustrative embodiment of an endodontic activator made in accordance with the present invention with a coupler portion of the activator being shown in cross-section.
FIG. 1A is a side elevational view of the endodontic activator mounted to a sonic vibratory driver.

The following detailed description illustrates the invention by way of example and not by way of limitation. This description will clearly enable one skilled in the art to make and use the invention, and describes several embodiments, adaptations, variations, alternatives and uses of the invention, including what is presently believed to be the best mode of carrying out the invention. Additionally, it is to be understood that the invention is not limited in its application to the details of construction and the arrangements of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

An illustrative endodontic activator or tip 10 (shown generally in FIG. 1) includes a generally cup-shaped hollow guard 12 at the proximal end thereof, a snap-on coupler 14 below the guard 12 and an active portion 16 extending from the coupler 14. As will be described more fully below, the active portion 16 is sized to be received in the root canal of a tooth during and after a root canal preparation procedure, and to extend to the full length of the root canal.

Figure 2:
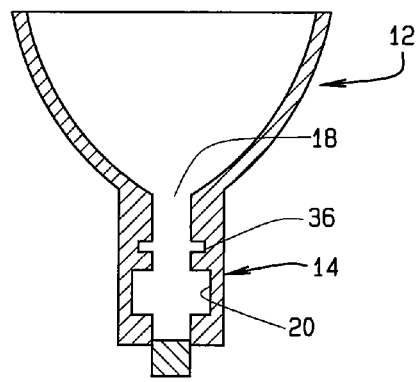
FIG. 2 is a cross-sectional view of a proximal end of the activator, showing the guard and the connector which enables the device to be connected to a driver.

As seen in FIG. 2, the hollow guard 12 is essentially cup-shaped and has an opening 18 at the bottom thereof. The opening 18 leads into the connector 14. The guard 12 and coupler 14 are sized and shaped to receive the end of a sonic driver D (FIG. 1A) which will vibrationally drive the activator 16 and produce a wave of oscillation along the overall length of the activator. The driver can, for example, be a driver as shown and described in U.S. Pat. No. 7,261,561, entitled "Vibrational Driver For Endodontic Activators" and which is incorporated herein by reference. The cup-shaped guard forms a shield about the driver during use to reduce the amount of fluids or aerosols that will spray against the driver during use and to consolidate the sterile protective barrier during use to improve vision.

The coupler 14 is adapted, sized and shaped to removably engage an arm of the driver which moves or oscillates when the driver is activated. As shown in FIGS. 1 and 2, the coupler 14 includes a recess 20 which can receive the arm of the driver to directly connect the activator 10 to the driver. The recess 20 can comprise one or more discrete holes, depressions, notches, etc. spaced about the inner circumference of the coupler (as shown in the figures) or a continuous circumferential groove. Alternatively, the recess 20 could be replaced with a rib or series of discrete projections or even spring mounted pins or balls, which would then be received in a groove or series of notches/indentations in the driver tip. The "snap" connection provided by the coupler 14 is advantageous because it allows for mounting and dismounting of the activator 10 from the driver without the use of tools. However, the activator 10 can be directly connected to the driver via other means as well. For example, a screw-type connection or a chuck-type connection can be used.

The activator's active portion 16 has a working portion 22 having length of about 16 mm. The active portion 16 can also include a section 24 extending between the coupler 14 and the working portion 22. The active portion 16 generally has an overall length of about 22 mm. The active portion defines a diameter $D_0$ at the distal tip thereof and a diameter $D_{16}$ at the upper end of the working portion 22. The working portion 22 can have generally straight sides but is preferably tapered. The working portion can be cylindrical, square, rectangular, triangular, or paddle shaped; and each of these shapes can then be either generally straight or tapered. The working portion 22 has a distal tip $D_0$ diameter of between about 0.1 mm and 0.2 mm, and $D_{16}$ diameter of between about 1.0 mm and about 1.5 mm, and a most proximal end $D_{22}$ diameter of about 2.0 mm. The taper of the working portion 22 can be between about 0.01 mm/mm and about 0.12 mm/mm (i.e., between about 1% and about 12%).

The active portion 16, as noted above, is preferably about 22 mm in length. Other shorter or longer lengths of the active portion 16 can be provided for, if desired. The active portion 16, from $D_{16}$ to $D_{22}$ (i.e., portion 24 of the active portion 16) can be generally cylindrical. Alternatively, this portion 24 can continue the taper of the working portion 22.

The activator 10 can be made available in multiple tip sizes and tapers, such as small, medium, and large, to cover variations of fully shaped canals following root canal preparation procedures. Additionally, the overall length of the activators can vary to address the variations in the working lengths of teeth. For example, the activators can be about 18 mm, about 22 mm and up to about 31 mm in overall length. Thus, for example, the small activator can have a $D_0$ tip diameter of about 0.1 or 0.2 mm and a $D_{16}$ diameter of about 0.52 mm; the medium activator can have a $D_0$ tip diameter of about 0.3 mm and a $D_{16}$ diameter of about 0.94 mm; and the large activator can have a $D_0$ tip diameter of about 0.5 mm and a $D_{16}$ diameter of about 1.5 mm. These specifications are examples of three possible combinations of size (diameter), taper and length. Of course, the specifications of the working portion 22 can vary to accommodate different sizes, tapers, and lengths of root canals. Thus, the $D_0$ diameter can be as large as 1.5 mm and the $D_{16}$ diameter can be as larger as 2 mm. The portion 24 of the active portion 16 from $D_{16}$ to $D_{22}$, at the bottom of the coupler 14, as noted above, can either continue to taper or be generally cylindrical. The active portion 16 can be permanently fixed to the snap-on coupler 14, which in turn is attached to the guard 12. The three activators (i.e., small, medium and large) each have different diameters and tapers and are provided as a set. Each activator comprises a proximal guard 12, a snap-on coupler 14, and an active portion 16. The different activators 10 in a set of activators can then be used as needed, as will be described further below.

At least the active portion 16 is formed from a strong, highly flexible, smooth, non-metallic and non-cutting material. The active portion 16 is shown in FIG. 1 in a bent or curved position. This is to show some of the flexibility of the active portion 16. In fact, the active portion 16 is sufficiently flexible to be bent into a U-shape. The activator 10 is made from a non-metal material, as noted, and can be made from a variety of polymers such as nylon, Delrin®, or an aromatic polyamide containing elastomers, such as are available from E. I. du Pont de Nemours and Company under the name Kevlar®. Activators made from Delin®, for example, have been manufactured with different $D_0$ diameters and tapers to provide a strong, highly flexible working portion 22 that can safely pass through canals that exhibit multiplanar curvatures. The overall diameter of the activator at its most distal end is less than the diameter of the apical end of the root canal such that the distal end of the activator can oscillate or move within the canal in a plane generally perpendicular to the axis of the canal when the activator is fully inserted in the root canal. Further, the overall diameter of the activator at its most distal end is sized such that the activator can achieve $2\alpha$ amplitude when the activator is sonically activated of vibrated.

The working portion 22 has a smooth surface. However, if desired, the surface of the activating portion can be flocked and/or textured to make the activating portion brush-like.

The activator 10, as noted above, is adapted at its proximal end to receive the arm of a sonic driver which extends through the guard 12 and into the coupler 14 to be directly connected to the arm of the driver or handpiece D. The driver arm is driven by a sonic generator. Evidence-based research has shown that the EndoActivator® handpiece in combination with the activator 10, both of which are commercially available from Dentsply International, produce statistically significantly cleaner root canal systems as compared to other commonly employed methods, including ultrasonics. This handpiece/driver is described in the above noted U.S. Pat. No. 7,261,561, entitled "Vibrational Driver For Endodontic Activators" and which is incorporated herein by reference.

When the working portion 22 is inserted into a fluid-filled and shaped root canal, and the driver is activated, the sonic energy of the driver will cause the flexible working portion 22 to vibrate or oscillate in the fluid in the root canal.

As is known, sonic energy and ultrasonic energy are produced by two very different technologies, and are substantially different in their effects. Sonic energy operates at a frequency up to about 15,000 cpm (cycles per minute), which is equivalent to about 250 cps (cycles per second). Ultrasonic energy, on the other hand, operates at frequencies between about 25000 and about 40000 cps. Importantly, sonic energy generates significantly larger amplitudes than does ultrasonic energy.

Moreover, the oscillating patterns of the sonically driven instruments are different from ultrasonically driven instruments. A minimum oscillation of the amplitude might be considered a node, whereas a maximum oscillation of the amplitude represents an anti-node. Sonically activated devices have only one node near the attachment of the tool to the driver and one anti-node at the tip of the tool where there is a maximum amplitude. Because of the single node and anti-node characteristic of sonic energy, the back and forth oscillation of the tip will not be dampened if any part of the active portion 16 contacts the root canal wall. Thus, regardless of the contact of the active portion 16 with the root canal wall, the tip of the active portion will fully vibrate or oscillate and will vibrate or oscillate at the sonic speed generated by the driver. Thus, when the sonic driver is operated, the working portion 22 can vibrate between about 10,000 cpm to about 15,000 cpm (or about 160-250 cps). Because the vibratory energy will not be dampened when side surfaces of the activator contact the root canal wall, the sonic energy selected will reach the most distal end or tip of the active portion 16 to desirably move or oscillate the tip of the active portion 16. The moving and oscillating working portion of the activator fractures any given intracanal irrigant or solution. At the fractured liquid interface, bubbles form that are unstable due to both heat and pressure, and clinically, each single bubble first expands and then implodes, sending out about 40,000 shock waves. It is the bombardment of the fluid within a relatively small space that produces fluid movement, penetration of the fluid into all aspects of the root canal system, and disinfection. As an example, shock waves remove the smear layer from the walls of the prepared root canal. Importantly, the mechanism of action of sonic energy along the activator 16 has been viewed histologically, and has been found to effectively debride pulp tissue and disrupt dentinal debris and biofilms from the lateral anatomy of the root canal system, thus effectuating a deep cleaning of the root canal system.

This is to be compared with ultrasonic activation. Ultrasonically operated instruments have a characteristic pattern of multiple nodes and antinodes along their length—that is, there are a plurality of nodes and a plurality of anti-nodes along the length of the tool. When an instrument is ultrasonically activated, it will vibrate at a frequency of about 25,000-40,000 cps. As noted above, because of the multiple nodes and anti-nodes along the length of an ultrasonically activated instrument (as compared to the single node and anti-node of a sonically activated instrument), the vibrations are dampened when the ultrasonically vibrated instrument contacts a surface along its length. Thus, an ultrasonically driven instrument does not move or oscillate as effectively as compared to a sonically driven instrument. Like a pendulum, an ultrasonically activated instrument produces angular displacement as it moves through back and forth cycles. The angle formed between a node and anti-node may be termed alpha ($\alpha$); and the angle formed between the peak and valley of successive anti-nodes is considered $2\alpha$, or the total range of back and forth movement. Hence, despite the fact that ultrasonic energy produces substantially higher frequencies, the fact remains that when the ultrasonically activated instrument contacts any given wall of the root canal preparation, its amplitude is dampened and $2\alpha$ is decreased. When an ultrasonically activated instrument looses its back and forth displacement, then the intracanal reagent/solution is not effectively activated, and disinfection will be compromised.

Figure 8A:
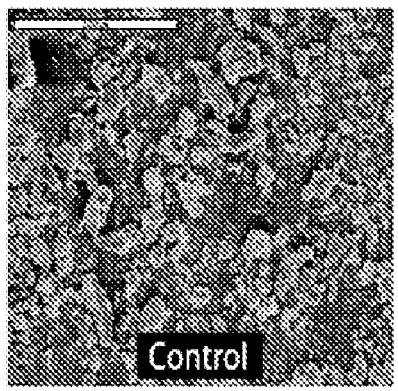
FIGS. 8A-C are photomicrographs comparing the removal of loose debris 3 mm from the radiographic apex of a canal via irrigation without activation (FIG. 8A) ultrasonic activation (FIG. 8B) and sonic activation (FIG. 8C).
Figure 8B:
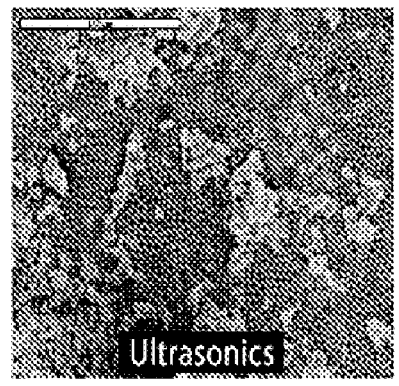
Figure 8C:
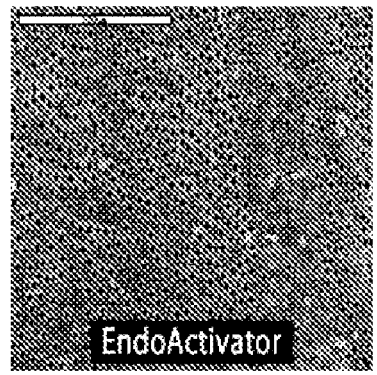

Using the same exact interval of time, the effect of sonic vs. ultrasonic activation is evident from representative photomicrographs of FIGS. 8A-C. FIG. 8A is a photomicrograph of a canal that was flushed with an irrigating solution, but without activation; FIG. 8B is a photomicrograph of a canal that was flushed with the same irrigating solution and wherein the irrigating solution was activated by means of an ultrasonically activated metal file; and FIG. 8C is a photomicrograph of a canal that was flushed with the same irrigating solution and wherein the solution was activated using a sonically driven nonmetal activator 10. As can be seen by comparing the three photomicrographs, while the ultrasonically activated tool removed some of the loose debris in the canal; the sonically activated activator 10 did a statistically significantly better job of removing debris from the root canal wall.

Because the active portion 16 is very strong and flexible, the sonic vibrations (i.e., sonic oscillations) induced in the active portion 16 by the sonic driver will induce hydrodynamic action of the solution within the root canal. This phenomenon will dislodge and remove the smear layer from the prepared walls of the canal, as described above and, further serve to provide a technique for deep lateral cleaning into all aspects of the root canal system. To maximize the hydrodynamic motion, the canal should be filled with an irrigating solution, such as sodium hypochlorite, EDTA, as discussed above, or other rinse solutions. The active portion 16 of the activator 10 is shaped such that when the activator is activated within a root canal filled with an irrigating solution, the vibrations along the length of the active portion 16 within the root canal will cause the formation of bubbles, as described above, which become unstable and implode, producing countless shock waves in the solution. Agitating the intracanal irrigant by sonically driving the activator as noted above produces a well-known hydrodynamic phenomenon which causes the intracanal irrigating solution to become turbulent, disrupting the smear layer and promoting deep lateral cleaning within the root canal system.

Stated differently, by energizing the flexible, non-cutting, and non-metallic active portion 16 at sonic speeds, the turbulence produced within the irrigating solution will enhance the effectiveness of the irrigating solution. Intracanal fluid activation produces bubbles that, as noted above, expand, implode, and produce shock waves that bombard the walls of the canal and serve to clean the inaccessible areas of the root canal system. Additionally, as the working portion 16 sonically vibrates within the root canal, its lateral walls will contact and rub against the surfaces of the root canal to physically enhance the chemical action of the irrigating solution. This non-cutting action will result in a better removal of the smear layer within the root canal than can be accomplished with, for example, vibrating cutting or non-cutting metal files. Further, because sonic energy is used, the contact between the working portion 16 and the lateral dentinal walls of the root canal will not dampen the vibrations, and the end of the working portion will move fully producing the desired $2\alpha$ amplitude. Additionally, because the activator is made from a non-metallic and non-cutting material, as noted above, the physical action of the tool within the root canal will not damage the internal walls of the canal. Specifically, the use of the activator 10 will not result in apical transportation or ledge formation within the canal, which can occur when using stiffer devices, such as vibrated/activated metal files or cannuli. Further, this method of cleaning will reduce the possibility of other iatrogenic events, such as perforations and broken instruments.

Figures 3, 4, 5:
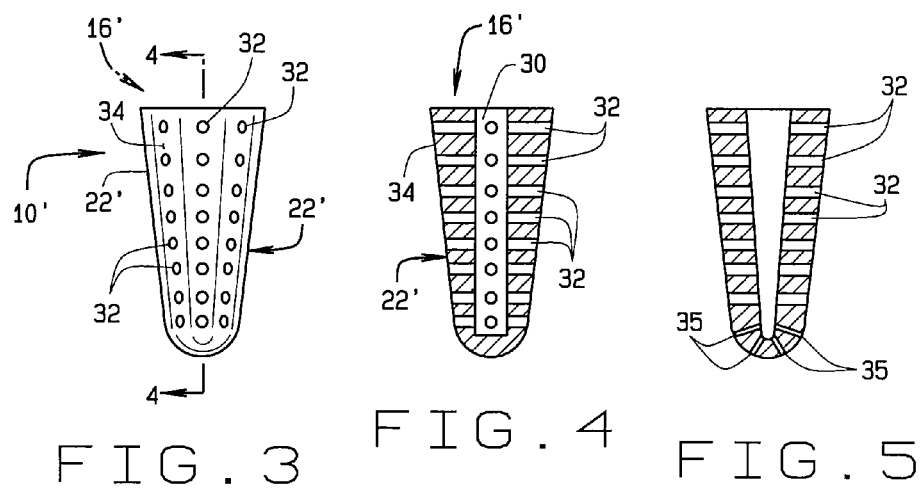
FIG. 3 is an enlarged fragmentary elevational view of an apical or distal end of a second illustrative embodiment of the endodontic activator, showing the working portion of the activator provided with a fluid flow passage and pores.
FIG. 4 is an enlarged cross-sectional view taken along line 4-4 of FIG. 3.
FIG. 5 is an enlarged cross-sectional view of the working portion of the activator showing a variation of the flow passage of FIGS. 3 and 4.

In another embodiment, the activator 10' (FIGS. 3-4) can be provided with a flow path defined in part by an axial or central flow channel 30, which extends through the working portion 22' and at least a part of the portion above the working portion 22' (not shown in FIG. 3 or 4). The flow channel 30, as shown, does not extend to the most distal end or tip of the active portion 16, but rather ends short of the distal end, as seen in FIG. 4. A plurality of small openings or pores 32 extend from the lateral surfaces 34 of the working portion 22' to the central flow channel 30 to complete the flow path. The pores 32 are shown to extend generally radially, but could extend from the lumen 30 at some other desired angle. These pores are located only in the working portion 22 of the active portion 16', and thus are formed only between the diameters $D_0$ and $D_{16}$ of the active portion 16' of the activator 10'. The more proximal portion 24 of the active portion 16' (i.e., between $D_{16}$ and $D_{22}$), in general, will not extend into a root canal and will be free of pores.

The sizes of the channel 30 and the pores 32 are determined in part by the size of the activator 10. The channel 30 can have a diameter of between about 0.1 mm and about 0.5 mm. The pores 32 have a diameter smaller than the diameter of the channel 30. The pore diameter can be between 0.001 mm and about 0.2 mm.

The pores 32, as seen in FIGS. 3 and 4, do not extend to the very distal end of the activating portion 22. Rather, they end short of the very distal end. For example, the pores can be absent from the region between $D_0$ and $D_1$.

However, as seen in FIG. 5, pores 35 can be formed to extend from the end of the lumen 30 to the activator surface between $D_0$ and $D_1$ (i.e., the area which is void of pores 32). The pores 35 can be the same size as the pores 32, or can be smaller or larger than the pores 32. For example, the pores 35 can be as small as 0.001 mm (1 micron).

The working portion 22' is shown to have a plurality of pores which exit laterally from the side of the working portion or near the bottom of the working portion. As shown in FIGS. 6A-B, the active portion 16" could, instead, be provided with a flow channel 30" which exits either at the most distal end of the active portion 16" (FIG. 6A) or along the side or lateral of surface 34 (FIG. 6B) of the active portion. If this single channel exits from the side or lateral surface of the active portion, the fluid flow path defined by the channel 30" and the exit channel would generally be L-shaped. It will be appreciated that such an L-shaped flow path need not define an angle of 90°. Rather, the bend in the flow path can define any angle. If the flow channel exits just proximal to the distal end of the activator, the fluid flow path can be generally straight or have a slight curvature near the bottom. Because there is only a single exit opening (as compared to the plurality of pores 32, 35 of the active portion 16'), the exit can have a diameter that is generally equal to the diameter of the channel 30". Alternatively, this single exit could have a diameter, as described above, which is smaller than the diameter of the channel 30".

As noted above, the flow channel 30 extends at least through a part of the activator portion 24, to enable the activator to be connected to a source of irrigant. In one embodiment, the channel 30 can extend through the active portion 16 and open into the coupler 14. The snap-on coupler 14 of the tool, in turn, is constructed to be connected to a source of irrigant, which can be associated with the driver (or to which the drive is connected). In addition, the coupler can be connected to a vacuum source which is also associated with the driver (or to which the driver is connected). To provide for a fluid tight seal between the coupler 14 and the driver, a groove 36 (FIG. 2) can be provided to receive an O-ring. Alternatively, the O-ring or other seal can be provided on the driver. The O-ring will form a liquid-tight seal between the tool connector and the liquid output from the drive. Thus, in addition to sonically vibrating the active portion 16', 16", the driver will also deliver irrigant through the channel 30, 30" and, when present, out through the pores 32 (and pores 35 if provided). In general, the irrigant will exit distally or alternatively along the lateral sides of the working portion 22', or depending on the construction of the activator, the irrigant may exit as a mist or droplets through the smaller pores 35 extending from the lumen 30 to the most distal aspect of the activating portion. Thus, during the irrigating procedure, as described above, the root canal will be supplied with fresh irrigant during the irrigating process to replace used irrigant. When energized by the driver, the working portion 22 of the tool 10 produces fluid hydrodynamics, which are optimized in a canal filled with fresh irrigant. Additionally, if the activator is connected to a handpiece which provides for suction (or which in turn is connected to a suction source), spent solution can be vacuumed from the root canal through the lumen.

When the activator is used to suction irrigant and debris (i.e., pulp tissue remnants, dentinal mud, and/or bacteria) suspended in the irrigant from the root canal, the flow channel 30" of FIG. 6 is preferable due to the larger size of the channel opening. In the activating portion 16', the smaller ports 32 and 35 may get blocked by the matter suspended in the irrigant solution.

A further embodiment of the activator is shown in FIG. 7. The activator 10''', as can be seen, is a contra-angled activator. The activators 10 and 10' on the other hand are "straight" activators. The straight activators 10 and 10' are designed to be received on a contra-angled handpiece. The activator 10''', on the other hand, is designed to be received on a straight ultrasonic handpiece, such as is commercially available from Satelec, Obtura/Spartan, SybronEndo, etc. The structure and function of such handpieces are well-known to those skilled in the art and will not be described or shown herein.

The activator 10''' includes a coupler 14''' which is configured, as known in the art, to enable the activator 10''' to be mounted to a commercially available straight, ultrasonic handpiece, as just described. Thus, the coupler 14''' will have a threaded bore which allows the activator 10''' to be threaded onto an end of the handpiece. Additionally, the coupler includes at least some flat faces to enable the activator to be tightened down on the handpiece by the use of a wrench or similar tool. An active portion 16''' extends from the coupler 14''' and comprises a working portion 22''' and a connecting portion 24''' between the working portion 22''' and the coupler 14'''. The active portion 16''' is shaped, as seen in FIG. 7, to form a contra-angle. To this end, the connecting portion 24''' includes a portion 24a and a second portion 24b. The first portion 24a is generally co-axial with, and extends generally straight from, the end of the coupler 14''. The second portion 24b is angled upwardly relative to portion 24a, with respect to the drawing of FIG. 7. The angle between portions 24b and 24a can define an angle α. The working portion 22''' then extends forwardly and downwardly from portion 24b, and forms an angle β therewith of about 90°. The size of the angles defined by the active portion 16''' can vary, as is known to those skilled in the art. As with the activators 10 and 10', at least the active portion 16''' is made from a non-metal, non-cutting material, as described above in connection with the activator 10. The coupler 14''' is preferably made from the same material as the active portion 16''', but can be made from a different material, if desired. The active portion 16''' can be solid, as is the active portion 16, or can be provided with a flow passage in the same manner as the active portions 16'. (FIGS. 3-6)

As various changes could be made in the above constructions without departing from the scope of the invention, it is intended that all matter contained in the above description or shown in the accompanying drawings shall be interpreted as illustrative and not in a limiting sense. Although the activator is shown and described to be adapted to be snapped or threaded onto a sonic driver, the activator can be adapted to be connected or attached to the driver in other ways. For example, the activator can be adapted to be attached to the driver via a latch-type connection, a friction grip connection, a chuck-type connection, or any other type of connection which will enable the driver to induce vibrations in the activator portion of the activator tool. In addition, although the activator is described as being connected to the EndoActivator® driver, it could be connected to other sonic drivers as well. The working portion (22, 22', 22'') is shown to be circular in cross-section and tapered over its length. As noted above, the working portion can be generally straight (rather than tapered) and can be provided with other cross-sectional shapes, as may be desired. These examples are merely illustrative.

The invention claimed is:

1. A method for cleaning a root canal system of a tooth of a living patient prior to three-dimensional filling of the root canal system during an endodontic procedure; the method comprising;
preparing an access cavity in the patient's tooth;
exposing the orifice(s) of the root canal within the pulp chamber of the tooth;
negotiating, shaping and finishing the preparation of the root canal;
removing the pulp, smear layer, and if present, bacteria and related irritants from the root canal system;
placing an irrigating solution in the root canal;
inserting an activator into the solution-filled root canal, such that the activator reaches substantially to the working length of the root canal; the activator being made from a strong, highly flexible, non-cutting, non-metal material and having a substantially smooth outer surface; the activator having an overall diameter at its distal end less than the diameter of the apical end of the root canal such that the distal end of the activator to can oscillate within the canal when the activator is fully inserted in the root canal; and
sonically energizing the activator to oscillate at least the distal end of the activator within the root canal at sonic speeds to thereby agitate the solution in the root canal system.

2. The method of claim 1 wherein said activator includes a flow path, said flow path including a channel extending through at least a portion of the activator and having at least one portal on a surface of said activator; said method further including passing solution through the flow path.

3. The method of claim 2 wherein the step of passing solution through the flow path comprises introducing fresh solution into the root canal system.

4. The method of claim 2 wherein the step of passing solution through the flow path comprising vacuuming spent solution from the root canal system.

5. The method of claim 4 wherein the steps of irrigating, vacuuming, and oscillating the distal end of the activator can be done individually or in combination.

6. The method of claim 2 wherein said step of passing solution through the flow path occurs during the step of sonically energizing the activator.

7. The method of claim 1 wherein the step of oscillating at least the distal end of the activator within the root canal moves at least the distal end of the activator in a plane generally perpendicular to the axis of the canal.

8. The method of claim 1 wherein the overall diameter of the activator at its most distal end is sized such that the activator can achieve 2α amplitude when the activator is sonically energized.

9. The method of claim 1 wherein the step of sonically energizing the activator induces sonic vibrations in the activator, whereby the sonically vibrating activator fractures solution in the canal.

10. A method for enhancing deep lateral cleaning of a root canal system during an endodontic procedure; the method comprising:
accessing the root canal of a tooth;
removing the pulp, dentinal debris, and if present, bacteria and related irritants from the root canal;
placing an irrigating solution into said root canal;
placing an activator into the solution in the root canal; the activator being of a length to reach substantially to the working length of the root canal; the activator being made from a strong, highly flexible, non-cutting, material; the activator having an overall diameter at a most distal end less than a diameter of an apical end of the root canal to allow for oscillatory movement of the distal end of the activator within the canal when the activator is fully inserted in the root canal; and sonically vibrating the activator to oscillate at least the distal end of an activator within the irrigating solution in the root canal; whereby, the oscillation of the activator in the solution in the root canal agitates the solution in the root canal system sufficiently to induce deep lateral cleaning of the root canal system.

11. The method of claim 10, wherein the step of oscillating the activator comprises:
inducing sonic vibrations in the activator.

12. The method of claim 10 wherein said activator includes a flow path comprised of a channel extending through at least a portion of said activator and having at least one portal on a surface of said activator; said method further including passing solution through the channel.

13. The method of claim 12 wherein said step of passing solution through the channel of said activator occurs during the step of inducing vibrations in the activator.

14. The method of claim 12 wherein the step of passing solution through the channel comprises passing fresh solution into the root canal.

15. The method of claim 12 wherein the step of passing solution through the flow path comprising vacuuming spent solution from the root canal.

16. The method of claim 10 wherein the step of oscillating at least the distal end of the activator within the root canal moves at least the distal end of the activator in a plane generally perpendicular to the axis of the canal.

17. The method of claim 10 wherein the overall diameter of the activator at its most distal end is sized such that the activator can achieve $2\alpha$ amplitude when the activator is sonically energized.

18. The method of claim 10 wherein the step of sonically oscillating the activator induces sonic vibrations in the activator, whereby the sonically vibrating activator fractures solution in the canal.

19. A method for enhancing deep lateral cleaning of a root canal system during an endodontic procedure; the method comprising:
accessing the root canal of a tooth;
removing the pulp, dentinal debris, and if present, bacteria and related irritants from the root canal;
placing an irrigating solution into said root canal;
placing an activator into the solution in the root canal; the activator being of a length to reach substantially to the working length of the root canal; the activator being made from a strong, highly flexible, non-cutting, material; the activator having an overall diameter at a most distal end less than a diameter of an apical end of the root canal to allow for oscillatory movement of the distal end of the activator within the canal when the activator is fully inserted in the root canal; the diameter of the activator being sized to enable the activator to achieve $2\alpha$ amplitude when the activator is sonically energized; and
sonically vibrating the activator to sonically oscillate at least the distal end of an activator within the irrigating solution in the root canal; whereby, the sonically vibrated activator fractures solution in the canal to generate shock waves in the solution.

* * * * *